US007189842B2

(12) United States Patent
Halverson et al.

(10) Patent No.: US 7,189,842 B2
(45) Date of Patent: Mar. 13, 2007

(54) HIGH DENSITY, MINIATURIZED ARRAYS AND METHODS OF MANUFACTURING SAME

(75) Inventors: Kurt J. Halverson, Lake Elmo, MN (US); Sanjay L. Patil, Aliso Viejo, CA (US); Jerald K. Rasmussen, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 684 days.

(21) Appl. No.: 10/167,204

(22) Filed: Jun. 11, 2002

(65) Prior Publication Data

US 2007/0021602 A1    Jan. 25, 2007

Related U.S. Application Data

(60) Continuation of application No. 10/060,799, filed on Jan. 30, 2002, now Pat. No. 6,841,258, which is a division of application No. 09/287,379, filed on Apr. 7, 1999, now Pat. No. 6,376,619, which is a continuation-in-part of application No. 09/059,427, filed on Apr. 13, 1998, now abandoned.

(51) Int. Cl.
*C07H 21/00* (2006.01)

(52) U.S. Cl. .................. 536/25.3; 422/50; 422/68.1; 435/6

(58) Field of Classification Search .............. 536/25.3; 422/50, 68.1; 435/6
See application file for complete search history.

(56) References Cited

U.S. PATENT DOCUMENTS

| | | | |
|---|---|---|---|
| 3,853,467 A | 12/1974 | Giaever | 23/230 |
| 3,926,564 A | 12/1975 | Giaever | 23/259 |
| 3,949,117 A | 4/1976 | Jvirblis et al. | |
| 4,190,757 A | 2/1980 | Turpin et al. | 219/10 |
| 4,266,108 A | 5/1981 | Anderson et al. | 219/10 |
| 4,304,705 A | 12/1981 | Heilmann et al. | |
| 4,451,619 A | 5/1984 | Heilmann et al. | |
| 4,485,236 A | 11/1984 | Rasmussen et al. | |
| 4,923,901 A | 5/1990 | Koester et al. | |
| 4,962,000 A | 10/1990 | Emslander et al. | 428/461 |
| 4,985,300 A | 1/1991 | Huang | 428/332 |
| 5,128,504 A | 7/1992 | McGaffigan et al. | 219/10 |
| 5,143,854 A | 9/1992 | Pirrung et al. | |
| 5,148,196 A | 9/1992 | Spector | |
| 5,149,806 A | 9/1992 | Moren et al. | |
| 5,165,965 A | 11/1992 | Martin | |
| 5,200,471 A | 4/1993 | Coleman et al. | |
| 5,202,231 A | 4/1993 | Drmanac et al. | |
| 5,204,219 A | 4/1993 | Van Ooij et al. | |
| 5,217,492 A | 6/1993 | Guire et al. | |
| 5,258,041 A | 11/1993 | Guire et al. | |
| 5,258,596 A | 11/1993 | Fabish et al. | 219/10 |
| 5,262,484 A | 11/1993 | Coleman et al. | |
| 5,278,377 A | 1/1994 | Tsai | 219/759 |
| 5,314,749 A | 5/1994 | Shah | |
| 5,317,045 A | 5/1994 | Clark, Jr. et al. | 523/300 |
| 5,344,701 A | 9/1994 | Gagnon et al. | |
| 5,403,902 A | 4/1995 | Heilmann et al. | |
| 5,428,209 A | 6/1995 | Babu et al. | 219/730 |
| 5,429,807 A | 7/1995 | Matson et al. | |
| 5,429,856 A | 7/1995 | Krueger et al. | |
| 5,436,147 A | 7/1995 | Pegg et al. | |
| 5,445,934 A | 8/1995 | Fodor et al. | |
| 5,446,270 A | 8/1995 | Chamberlain et al. | 219/730 |
| 5,464,900 A | 11/1995 | Stofko, Jr. et al. | |
| 5,474,796 A | 12/1995 | Brennan | |
| 5,500,251 A | 3/1996 | Burgoyne, Jr. et al. | |
| 5,501,679 A | 3/1996 | Krueger et al. | |
| 5,525,464 A | 6/1996 | Drmanac et al. | |
| 5,529,708 A | 6/1996 | Palmgren et al. | 252/62 |
| 5,541,057 A | 7/1996 | Bogart et al. | 435/5 |
| 5,552,270 A | 9/1996 | Khrapko et al. | |
| 5,554,501 A | 9/1996 | Coassin et al. | |
| 5,562,958 A | 10/1996 | Walton et al. | |
| 5,583,211 A | 12/1996 | Coassin et al. | |
| 5,597,405 A | 1/1997 | Grigoryan et al. | 106/20 |
| 5,601,980 A | 2/1997 | Gordon et al. | |
| 5,602,202 A | 2/1997 | Groves | |
| 5,607,107 A | 3/1997 | Grieve et al. | 239/195 |
| 5,620,780 A | 4/1997 | Krueger et al. | |
| 5,620,803 A | 4/1997 | Oyama et al. | |
| 5,639,546 A | 6/1997 | Bilkadi | |
| 5,658,625 A | 8/1997 | Bradfute et al. | |
| 5,658,802 A | 8/1997 | Hayes et al. | |
| 5,691,034 A | 11/1997 | Krueger et al. | |

(Continued)

FOREIGN PATENT DOCUMENTS

GB     2 065 298 A     6/1981

(Continued)

OTHER PUBLICATIONS

Article: O'Donnell-Maloney et al., "Microfabrication and Array Technologies for DNA Sequencing and Diagnostics," *Genetic Analysis: Biomolecular Engineering*, vol. 13 (1996) pp. 151-157.

(Continued)

*Primary Examiner*—Bernard Lipman
(74) *Attorney, Agent, or Firm*—Nancy M. Lambert

(57) ABSTRACT

High-density, miniaturized arrays including high surface areas. Arrays described include substrate with a coating of linking agents, as well as arrays with reactants affixed to the substrates. Methods of manufacturing high-density arrays of reactants. The methods include the use of oriented, heat shrink films and elastomeric materials. Methods of functionalizing a substrate with linking agents for subsequent affixation of reactants are also disclosed herein.

19 Claims, 7 Drawing Sheets

U.S. PATENT DOCUMENTS

| | | | |
|---|---|---|---|
| 5,695,940 A | 12/1997 | Drmanac et al. | |
| 5,720,834 A | 2/1998 | Steele et al. | 156/86 |
| 5,744,305 A | 4/1998 | Fodor et al. | |
| 5,750,245 A | 5/1998 | Exsted et al. | |
| 5,757,458 A | 5/1998 | Miller et al. | |
| 5,770,721 A | 6/1998 | Ershov et al. | |
| 5,773,374 A | 6/1998 | Wood et al. | |
| 5,800,903 A | 9/1998 | Wood et al. | |
| 5,840,412 A | 11/1998 | Wood et al. | |
| 5,858,653 A | 1/1999 | Duran et al. | |
| 5,916,203 A | 6/1999 | Brandon et al. | 604/367 |
| 5,925,455 A | 7/1999 | Bruzzone et al. | 428/328 |
| 6,013,789 A | 1/2000 | Rampal | 536/25 |
| 6,063,484 A | 5/2000 | Exsted et al. | |
| 6,070,579 A | 6/2000 | Bryant et al. | |
| 6,156,478 A | 12/2000 | Liu et al. | 430/270 |
| 6,245,518 B1 | 6/2001 | Baier | |
| 6,344,271 B1 | 2/2002 | Yadav et al. | 428/402 |
| 6,376,619 B1 | 4/2002 | Halverson et al. | |
| 6,376,719 B1 | 4/2002 | Okada | 568/412 |
| 6,395,483 B1 | 5/2002 | Patil et al. | |
| 6,593,089 B2 | 7/2003 | Patil et al. | 435/6 |
| 6,664,060 B2 | 12/2003 | Patil et al. | 435/6 |

FOREIGN PATENT DOCUMENTS

| | | |
|---|---|---|
| JP | 10-0254362 | 9/1998 |
| WO | WO 94/16803 | 8/1994 |
| WO | WO 95/04834 | 2/1995 |
| WO | WO 95/11912 | 5/1995 |
| WO | WO 97/27329 | 7/1997 |
| WO | WO 97/43447 | 11/1997 |
| WO | WO 97/44134 | 11/1997 |
| WO | WO 98/45406 A1 | 10/1998 |
| WO | WO 99/53319 A2 | 10/1999 |
| WO | WO 99/53319 A3 | 10/1999 |

OTHER PUBLICATIONS

Article: Guo et al., "Direct Fluorescence Analysis of Genetic polymorphisms by Hybridization with Oligonucleotide Arrays on Glass Supports," *Nucleic Acids Research,* vol. 22, No. 24 (1994) pp. 5456-5465.

Article: O'Donnell-Maloney et al., "The Development of Microfabricated Arrays for DNA Sequencing and Analysis,", *Tibtech,* vol. 14 (Oct. 1996) pp. 401-407.

Product Information: "Cryovac® D-955 Film," Cryovac Division, W.R. Grace & Co., (date unknown) two pages.

Martynova, L. et al.; "Fabrication of Plastic Microfluid Channels by Imprinting Methods"; Analytical Chemistry; vol. 69, No. 23, Dec. 1, 1997; p. 4783-4789.

Schena, M. et al.; "Parallel human genome analysis: Microarray-based expression monitoring of 1000 genes"; Proc. Natl. Acad. Sci.; vol. 93, Oct. 1996; Biochemistry; pp. 10614-10619.

Freifelder, D.; "Physical Biochemistry—Applications to Biochemistry and Molecular Biology" 2nd Edition; W.H. Freeman and Company; 1982; pp. 496-498.

HIGH DENSITY, MINIATURIZED ARRAYS AND METHODS OF MANUFACTURING SAME

This application is a continuation of U.S. patent application Ser. No. 10/060,799, filed Jan. 30, 2002 now U.S. Pat. No. 6,841,258, which is a divisional of U.S. patent application Ser. No. 09/287,379, filed Apr. 7, 1999 and now U.S. Pat. No. 6,376,619, which is a continuation-in-part of U.S. patent application Ser. No. 09/059,427, now abandoned.

GOVERNMENT NOTICE

This invention was made with government support under Project Number 95-08-0006 awarded by the National Institute of Standards and Technology. The government has certain rights in the invention.

FIELD OF THE INVENTION

This invention relates to arrays manufactured on polymeric surfaces and more particularly to high-density, miniaturized arrays and methods of manufacturing the same.

BACKGROUND

Miniaturized arrays may be used in a variety of applications, such as gene sequencing, monitoring gene expression, gene mapping, bacterial identification, drug discovery, and combinatorial chemistry. Many of these applications involve expensive and oftentimes difficult to obtain samples and reagents. Accordingly, high density, miniaturized arrays are desirable because the use of such arrays may dramatically increase efficiency with respect to limited or expensive samples when compared to standard arrays, such as a 96 well plate. For example, a 96 well plate may require several hundred microliters of sample per well to run a diagnostic experiment whereas a miniaturized array would require only a fraction of that sample for the entire array. In addition to the reduction of volume, miniaturization allows hundreds or thousands of tests to be performed simultaneously. Furthermore, a high-density array may be more versatile than a standard array because of the wide variation of chemistries that may be present on a single array.

Current methods of manufacturing miniaturized arrays are not conducive to mass production. These methods are limited by multiple step procedures and by the difficulty in achieving miniaturized arrays with densely packed reactants. The manufacture of arrays is further complicated in applications requiring different chemistries at different binding sites on the arrays, such as required for manufacturing oligonucleotide arrays.

One example of a multiple step procedure for manufacturing arrays is disclosed in U.S. Pat. No. 5,445,934. This patent discloses a method of on-chip synthesis. In this process, the substrate is derivatized with a chemical species containing a photocleavable protecting group. Selected sites are deprotected by irradiation through a mask. These sites are then reacted with a DNA monomer containing a photoprotective group. The process of masking, deprotecting and reacting is repeated for each monomer attached until an array of site-specific sequences is achieved. This process may be both time-consuming and resource intensive. Because of the planar nature of the surface, a limited concentration of oligonucleotides (measured by the distance between adjacent oligonucleotides within a binding site) can be synthesized at each binding site before steric crowding interferes with the hybridization reaction. As a result, the amount of detectable signal from each binding site may also be limited.

Another type of method used to manufacture arrays is off-chip synthesis. An example of off-chip synthesis is disclosed in U.S. Pat. No. 5,552,270. This process uses gel pads. The gel pads are created on a substrate using robotic devices. Thereafter, minute quantities of presynthesized oligonucleotides are robotically placed on individual gel pads on the substrate. Production of chips using off-chip synthesis is generally time-consuming because each solution is deposited individually or in small groups. High densities are difficult to achieve because of the limited resolution of robotic devices and the physical size limitations of the fluid delivery devices. This type of process typically requires the use of specialized, sophisticated, and miniaturized tools. The use of gel pads facilitates the affixation of a higher concentration of oligonucleotides within each binding site, which may overcome the difficulties encountered with planar surfaces outlined above. However, the use of thick gel layers hinders hybridization kinetics due to slow target analyte diffusion into and out of the gel.

SUMMARY

There is a need for high density, miniaturized arrays including reactive surfaces with high surface areas and high detection signal strength. Preferably, the arrays would facilitate rapid binding kinetics between affixed reactants and target analytes. There is a further need for methods of manufacturing high density, miniaturized arrays. The methods preferably would be cost-effective and amenable to mass production.

In one embodiment of the present, invention, an array includes a polymeric substrate and a coating comprising linking agents at least partially adhered thereto. The coating comprising linking agents has a projected surface area and a topographical surface area, and the topographical surface area is greater than the projected surface area. The topographical surface area is at least two times greater than the projected surface area. In a preferred embodiment, the topographical surface area is at least five times greater than the projected surface area. In a most preferred embodiment, the topographical surface area is at least fifteen times greater than the projected surface area. Preferably, the coating includes an undulated surface.

In a preferred embodiment of the present invention, the array includes a binding site density of over 1,000 binding sites per square centimeter. A density of at least 25,000 binding sites per square centimeter is preferred with a density of over 60,000 per square centimeter being most preferred.

In another embodiment of the present invention, a material for use in manufacturing an array includes an oriented, polymeric substrate including a coating comprising linking agents. This material is suitable for the subsequent affixation of reactants thereto.

The arrays of the present invention facilitate the affixation of a high concentration of reactants at each binding site, with all of the attendant advantages of high density, including the ability to increase detection signal strength. The high topographical surface area arrays are particularly useful in this regard. In addition, these high surface area arrays allow sample containing the analyte(s) of interest to rapidly come into contact with the reactants, without the necessity of diffusing into a thick coating, such as a hydrogel.

In one embodiment of the methods of the present invention, a polymeric substrate includes a major surface having a surface area. A reactant, such as DNA, is affixed to the major surface of the substrate to create binding sites. The surface area of the major surface is reduced, thereby increasing the density of binding sites on the substrate.

In a preferred embodiment, the substrate is a biaxially oriented, heat shrink film. In a particularly preferred embodiment of the present invention, the reactants are oligonucleotides wherein the oligonucleotides vary in composition at differing binding sites on the substrate.

In another method of the present invention, a heat shrink film is functionalized to create linking agents on the surface of the film for subsequent thereby increasing the density of linking agents on the substrate. Preferably, the heat shrink surface is functionalized with azlactone linking agents.

In yet another embodiment of the present invention, an elastomeric substrate is stretched and functionalized to create linking agents on the surface of the substrate. Reactants, such as DNA, may be affixed to the substrate via linking agents. The substrate is subsequently allowed to relax, thereby reducing the surface area of the substrate to increase the density of linking agents on the substrate. A backing or other structure may be added to retain the substrate in the reduced orientation.

In yet another embodiment of the present invention, a method of manufacturing arrays of the present invention includes providing an oriented polymeric substrate. A coating comprising linking agents is applied to a surface of the substrate. Subsequently, the substrate is relaxed such that it becomes less oriented or isotropic. During this relaxation step, the topographical surface area of the coating becomes greater than the projected surface area of the coating. Reactants may be affixed to the linking agents prior, during or subsequent to the relaxation step to create an array with binding sites. Preferably, the reactants are affixed prior to the relaxation step.

The methods of manufacture of the present invention are amenable to mass production. The methods of manufacture of the present invention may be employed to increase the efficiency of current methods of manufacture of arrays to achieve high densities of reactants. The methods of the present invention are particularly useful in achieving high-density nucleic acid arrays wherein different nucleic acids are located at different sites on the substrate.

Various other features and advantages of the present invention should become readily apparent with reference to the following detailed description, examples, claims and appended drawings.

DETAILED DESCRIPTION OF THE PREFERRED EMBODIMENTS

Figure 1A:
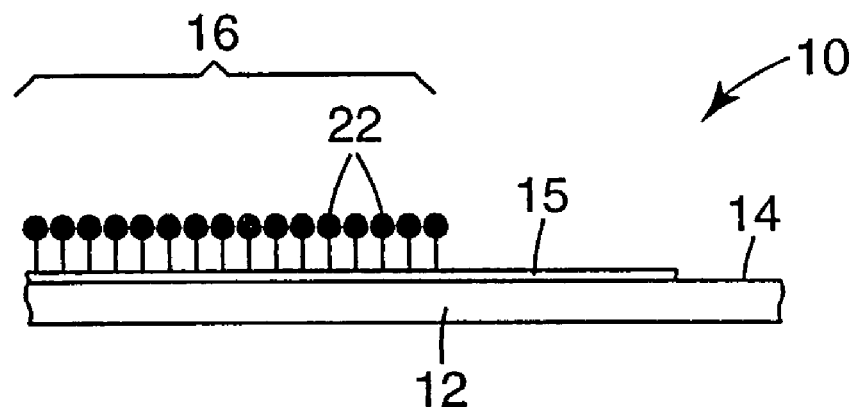
FIG. 1a is side view of an array of the present invention prior to relaxation of the substrate thereof.

The present invention provides high-density, miniaturized arrays and methods of manufacturing the same.

For purposes of this invention, the following definitions shall have the meanings set forth.

"Affix" shall include any mode of attaching reactants to a substrate. Such modes shall include, without limitation, covalent and ionic bonding, adherence, such as with an adhesive, and physical entrapment within a substrate. In the case of linking agents, reactants may be affixed to the substrate by linking agents that are created by functionalizing a surface, such as with an acid wash, or by linking agents that are coated on the substrate.

"Analyte" shall mean a molecule, compound, composition or complex, either naturally occurring or synthesized, to be detected or measured in or separated from a sample of interest. Analytes include, without limitation, proteins, peptides, amino acids, fatty acids, nucleic acids, carbohydrates, hormones, steroids, lipids, vitamins, bacteria, viruses, pharmaceuticals, and metabolites.

"Binding site" shall mean a discrete location on a substrate wherein reactants are affixed thereto. A single binding site may include a quantity of one or more of the same reactants affixed to the substrate.

"Density" shall mean a measure of quantity per unit projected area of substrate, such as, for example, linking agents per square centimeter or binding sites per square centimeter.

"Equivalent" shall mean substantially equal.

"Linking agent" shall mean any chemical species capable of affixing a "Reactant" to the substrate.

"Projected surface area" shall mean the surface area for a surface as is calculated with respect to the plane encompassing the "x" and "y" axes of the surface.

"Reactant" shall mean any chemical molecule, compound, composition or complex, either naturally occurring or synthesized, that is capable of binding an analyte in a sample of interest either alone or in conjunction with a molecule or compound that assists in binding the analyte to the substrate, such as, for example, a coenzyme. The reactants of the present invention are useful for chemical or biochemical measurement, detection or separation. Accordingly, the term "Reactant" specifically excludes molecules, Compounds, compositions or complexes, such as ink, that do not bind analytes as described above. Examples of reactants include, without limitation, amino acids, nucleic acids, including oligonucleotides and cDNA, carbohydrates, and proteins such as enzymes and antibodies.

"Topographical surface area" shall mean the surface area of a surface as is calculated with respect to the planes encompassing the "x, y" and "z" axes of the surface, or in other words, a measurement of the surface features of the coating.

"Undulations -or- undulated" shall mean convoluted, wave-like forms. For purposes of this invention, it is preferred that an undulated surface comprises undulations that are irregular as to pattern such as are depicted in FIGS. 6b, 7b, 8b and 9b. "Undulations -or- undulated" does not include structures such as reservoirs or microwells that are created by methods such as for example printing, embossing, casting, molding, laserscribing, photolithography, etching, mechanical scratching or scoring.

Figure 1B:
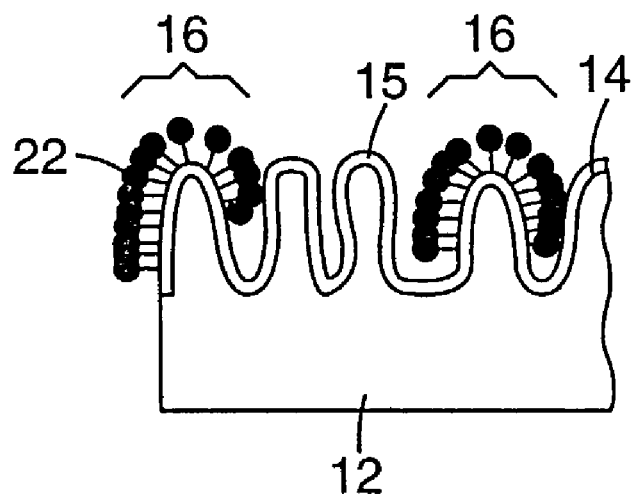
FIG. 1b is a side view of the array of FIG. 1a of the present invention subsequent to relaxation of the substrate thereof.

With reference to FIGS. 1a and 1b, the present invention 10 includes a substrate 12 with at least one major surface 14 having a surface area. The major surface 14 may be generally smooth or may include undulations. The substrate 12 may be any number of shapes. The shape of the substrate 12 is not limiting, so long as the substrate 12 provides a base for applying the coating 15 comprising linking agents and reactants 22 thereon, as described more fully below.

The substrate of the present invention is a polymeric material. The material of the substrate is selected with regard to the application for the resulting arrays. For example, the substrate preferably exhibits low background fluorescence in the event fluorescence is used for detection purposes and therefore will not substantially interfere with the indicator systems used in the assays run on the arrays manufactured in accordance with the methods of the present invention. The substrate material preferably is compatible with the reagents and conditions of the assays, such as temperature and pH.

Many polymeric materials may be suitable for use in the present invention. However, in order to form the high surface area surface of the linking agent coating, as described more fully below, the materials are preferably capable of being oriented, i.e., films that shrink at least in one direction within the film plane when energy, preferably heat, is applied to the film for a specified period of time. Elastomeric materials, which are stretched at least in one direction prior to affixation of reactants, constrained in the stretched state during affixation of reactants, and then allowed to recover, thereby reducing the projected surface area of the substrate surface from the stretched state, are also suitable for use in the present invention.

With respect to oriented films, shrinkage need not be equal in any two orthogonal directions within the film plane, although a substantially uniform shrinkage is preferred. In considering shrinkage as a function of direction in the film plane, substantial uniformity of directionally-dependent shrinkage from point to point within the film is preferred; that is, the film preferably shrinks in substantially the same amount in each direction, regardless of position on the film plane. If the film employed does not exhibit substantially uniform shrink characteristics, a registration indicator may be added to the binding sites or otherwise employed to register the binding sites in the finished array.

While the starting substrate material of the present invention includes oriented films, the substrates of the arrays of the present invention are generally relaxed, i.e., generally no longer oriented or, in fact, isotropic. A backing may be applied to the substrate to maintain the substrate in a less than oriented state. The backing may optionally include a release liner to permit the backing to be removed if desired.

The substrate provides a preferably non-porous surface upon which coatings and/or reactants may be affixed. Upon relaxation of the oriented substrate or reduction of the surface area of the major surface, the substrate provides support and integrity to the coatings and/or reactants thereon. In addition, the substrate maintains the relative spatial relationship of the binding sites.

Preferred oriented films include biaxially oriented low-density polyethylenes; biaxially oriented linear low-density polyethylenes; and biaxially oriented ultra low-density polyethylenes. Biaxially oriented films are preferred because they exhibit shrinkage in two orthogonal in-plane directions (hereafter referred to as the "x" and "y" directions). Other oriented films that may be suitable for use in the present invention include uniaxially, biaxially, or multiaxially oriented films made by any process known to the art, including but not limited to melt-orientation; the blown film, bubble, double-bubble, and tubular processes; length orientation; the process of tentering; extension over a mandrel; thermoforming; and blow molding. Polymers which may be employed in such films include, but are not limited to, polyethylenes, including high density polyethylene, low density polyethylene, linear low density polyethylene, ultra low density polyethylene, and copolymers of ethylene (including ethylene propylene copolymers and ethylene vinyl acetate copolymers); polyolefins, including isotactic polypropylene, syndiotactic polypropylene, and polymethylpentene; polyacetals; polyamides, including polyamide 6 and polyamide 66; polyesters, including polyethylene terephthalate, polybutylene terephthalate, and polyethylene naphthalate; halogenated polymers, including polyvinyl chloride, polyvinylidene chloride, polychlorotrifluoroethylene, polyvinyl fluoride, and polyvinylidene fluoride; styrene polymers, including general purpose polystyrene and syndiotactic polystyrene; cellulose esters, including cellulose acetate and cellulose propionate; polyketones, including polyetheretherketone and copolymers and terpolymers of carbon monoxide with ethylene and/or propylene; polycarbonates, including the polycarbonate of bisphenol A; phenyl-ring polymers, including polyphenylene sulfide; polysulfones; polyurethanes; polymers of acrylic and methacrylic acids and their esters; ionomers; and copolymers, blends, or layered structures of any of the above-named polymers. Oriented films of any of these polymers may be optionally cross-linked.

Examples of elastomeric materials that may be suitable for use in the present invention include natural rubber, polyisoprenes, polychloroprene, polyisobutylenes, polybutenes, nitrites, polyurethanes, silicones, random copolymers and terpolymers (such as ethylene-propylene copolymers and ethylene-propylene-diene monomer terpolymers), and block copolymers.

With continuing reference to FIGS. 1a and 1b, the array includes a coating comprising linking agents. The linking agents are selected based on the reactants 22 to be affixed to the substrate 12 and the application for which the array will be used.

Figure 6A:
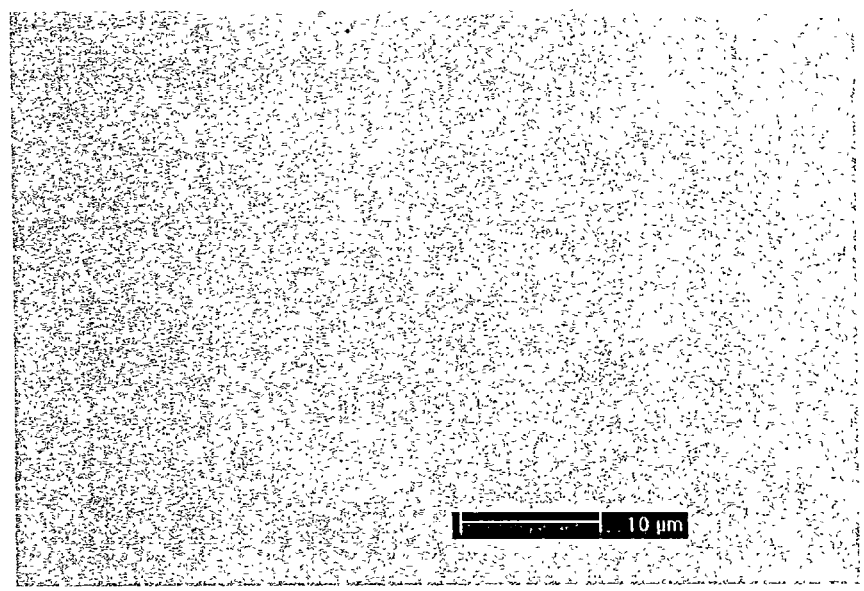
FIG. 6a is a scanning electron micrograph (SEM) of a substrate coated with a copolymer of dimethylacrylamide/vinyldimethylazlactone prior to relaxation of the substrate.
Figure 8A:
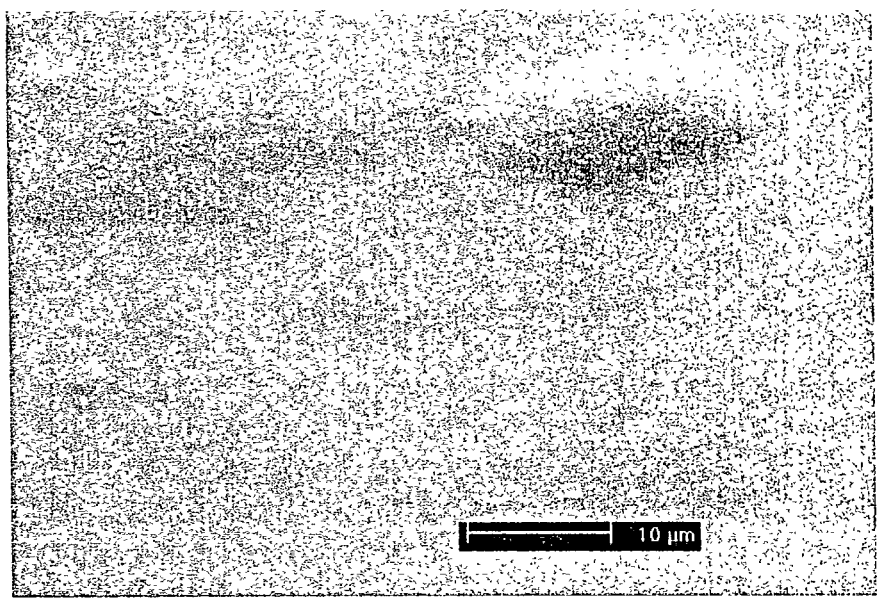
FIG. 8a is an SEM of a substrate coated with a carboxylated polyvinylchloride prior to relaxation of the substrate.

In a preferred embodiment, the linking agents are coated onto the major surface 14 of the substrate 12 such that the coating 15 is at least partially adhered to the substrate 12. The coating 15 comprising linking agents has a projected surface area and a topographical surface area. The coating on the substrate generally is smooth in appearance, such as depicted in FIGS. 6a and 8a. Accordingly, the projected surface area and the topographical surface area are substantially equivalent.

As described more fully below, upon relaxation of the substrate 12, the topographical surface area becomes greater than the projected surface area. Surprisingly, the arrays 10 of the present invention include coatings 15 that are capable of exhibiting topographical surface areas that greatly exceed the projected surface areas. The topographical surface area of the coating 15 is at least two times greater than the projected surface area of the coating. Preferably, the topographical surface area is at least five times greater than the projected surface area. In a most preferred embodiment, the topographical surface area is at least fifteen times greater than the projected surface area.

In a preferred embodiment, upon relaxation of the substrate 12, as explained more fully below, the coating of linking agents 15 becomes undulated as depicted in FIGS. 1b, 6b, 7b, 8b and 9b. While the undulations in these figures are irregular with respect to any discernable pattern, it is contemplated that a regular pattern of undulations may be achievable in accordance with the methods of the present invention.

It is believed that this quite unexpected result is due to a variety of factors, including the adhesion properties of the coating with respect to the substrate as well as the thickness and glass transition temperature ($T_g$) of the coating. Upon relaxation of the substrate, a stress mismatch will develop at the substrate/coating interface due to the strain match. The adhesion of the coating to the substrate should be sufficient to prevent total delamination of the coating from the substrate. Because the desired array preferably includes an undulated surface, a degree of delamination may actually occur and still provide a useful array in accordance with the present invention. However, the degree of delamination should not be so great as to interfere with assays being conducted on the arrays or result in effective loss of the coating from the substrate.

Significantly, the inventors of the present invention discovered that heating to relax the substrate may actually improve adhesion to the coating. It is possible that, due to the undulations, the polymeric substrate and the polymeric coating form an interlocking structure. In addition, some entanglement of polymer chains may occur at the substrate/coating interface during the heating step. In both instances, upon cooling, the interlocking structures or polymer entanglements may serve to minimize delamination of the coating.

It is believed that thicker coatings will result in larger-dimensioned undulations because the flexural rigidity of the coating will vary approximately as the cube of its thickness. In theory, a flexurally stiffer object would be expected to bend at a larger radius than that of an object of less rigidity (all other variables being equal). In practice, the flexural rigidity will also be affected by the adhesion properties of the coating with respect to the substrate.

In the present invention, a coating of between about 0.1 micron and 10 microns is preferred, with a coating of less than about 1 micron being preferred in order to minimize diffusion difficulties that may arise when using thicker coatings. An analyte of interest may have to diffuse through the coating prior to contacting a reactant affixed thereto. If the coating of linking agents is relatively thick, e.g. greater than about 10 microns, the diffusion time required could slow the kinetics of the analyte/reactant interaction. Furthermore, if the coating is too thick, it may delaminate from the substrate because of the high flexural rigidity of such a coating.

It is also believed that if the $T_g$ of the coating is substantially lower than the $T_g$ of the substrate, the coating will have sufficient time to undergo viscoelastic flow during reduction of the substrate surface upon which the coating is adhered. The resulting coating will be relatively smooth and lacking in significant undulations. In this instance, the projected surface area of the coating and the topographical surface area of the coating will be substantially equivalent. In addition, the coating will increase in thickness. On the other hand, it is surmised that coatings with a $T_g$ fairly comparable to or higher than that of the substrate will not undergo sufficient viscoelastic flow during the relaxation of the substrate and accordingly will result in an undulated surface having a high topographical surface area.

In light of the foregoing, it is believed that a wide variety of coatings may be suitable for use in the present invention, provided the coatings are suitable for affixing reactants and are compatible with the assays and attendant conditions that are to be conducted on the particular array. Preferred linking agents are azlactone moieties such as those provided by copolymers as taught in U.S. Pat. Nos. 4,304,705; 4,451,619; 5,262,484; 5,344,701; and 5,403,902; which are incorporated herein by reference. Especially preferred copolymers are those prepared using hydrophilic or water-soluble comonomers such as acrylamide and acrylamide derivatives, hydroxyethylacrylate and methacrylate, and the like. In addition to azlactone linking agents, copolymers including other linking agents may also be utilized. These include, for example, epoxy, carboxylic acid, hydroxyl, amine, N-hydroxysuccinimide, iso- and isothiocyanate, anhydride, aldehyde, and other groups which are well known in the art for the immobilization of reactants. The copolymers comprising linking agents may be prepared by either step growth or chain growth polymerization processes as are well known in the art.

Azlactone moieties are preferred because these moieties are suitable for reaction with numerous reactants, including oligonucleotides. Azlactone moieties are generally hydrolytically stable and therefore have a relatively long shelf life when used in applications of the present invention. These moieties also generally exhibit high reactivity with a wide variety of reactants.

The coatings may be crosslinked or otherwise treated to insolubilize, modify the $T_g$ or modify the adhesion properties of the coating. For example, copolymers that have a low $T_g$ may be formulated with a cross-linker in order to raise the $T_g$ of the resultant coating. The coatings can be applied to the substrate by any of several conventional means known in the art, such as extrusion coating, die coating, dip coating, air-knife coating, gravure coating, curtain coating, spray coating, use of wire wound coating rods, and the like. Coatings may be made from solution, followed by removal of solvent, or by hot melt coating of 100% solids formulations.

Adhesion of the coating to the substrate may be improved, if desired, by any of the methods known to one skilled in the art. These methods include various pre-treatments to or coatings on the major surface, such as corona or plasma treatment, or by application of primers. Suitable primers include, without limitation, polyethylenimine, polyvinylidenechloride, primers such as those described in U.S. Pat. No. 5,602,202, the disclosure of which is incorporated herein by reference, and colloidal dispersions of inorganic metal oxides in combination with ambifunctional silanes such as described in U.S. Pat. Nos. 5,204,219, 5,464,900, and 5,639,546, the disclosures of which are all incorporated herein by reference. Other methods of increasing adhesion of copolymers to polyolefin substrates are disclosed in U.S. Pat. No. 5,500,251, the disclosure of which is incorporated herein by reference.

The linking agents may be coated substantially over the entire area of a surface of the substrate, such as the major surface, or in spots that may be in a regular or irregular pattern on such surface. In the latter case, upon relaxation of the substrate, the topographical surface area of each spot will be greater than the projected surface area of such spot. Alternatively, more than one polymeric layer comprising linking agents may be coated on the substrate. A first coating of linking agents may be overcoated by a second coating comprising linking agents in order to obtain undulations in accordance with the methods of the present invention. In this manner, a coating that would otherwise not form undulations may be converted to an undulated coating. Preferably, the two coatings would adhere to each other or chemically bond to each other. For example, the substrate may be coated with a polymer including azlactone moieties that in turn is overcoated with a second polymer including amine moieties. The amines and azlactones would react to bind the layers together, however, it is anticipated that free amines groups would remain to affix reactants, such as cDNA, to the substrate.

Figure 3:
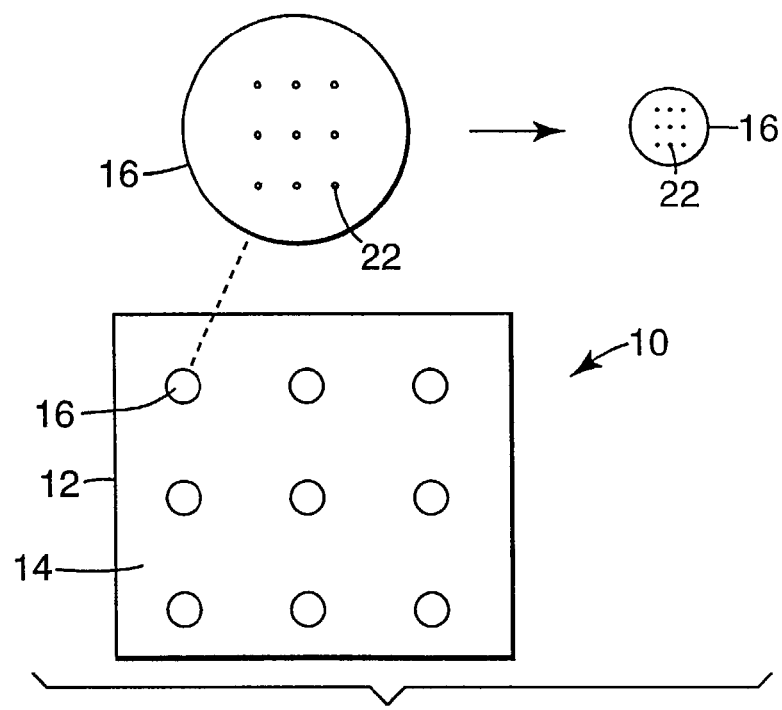
FIG. 3 is an exploded view of a binding site of an array manufactured in accordance with the methods of the present invention.

Reactants 22 are affixed to the substrate 12 to create binding sites 16 as depicted in FIGS. 1a, 1b and 3. As described more fully below, with respect to the methods of the present invention, any number of processes known in the art may be used to introduce the reactants to be affixed to the substrate. It is understood that the mode of affixation may vary in accordance with the reactant or reactants employed.

The type of reactant used in the present invention will vary according to the application and the analyte of interest. For example, when characterizing DNA, oligonucleotides are preferred. When conducting diagnostic tests to determine the presence of an antigen, antibodies are preferred. In other applications, enzymes may be preferred. Accordingly, suitable reactants include, without limitation, amino acids, nucleic acids, including oligonucleotides and cDNA, carbohydrates, and proteins such as enzymes and antibodies.

Figure 2:
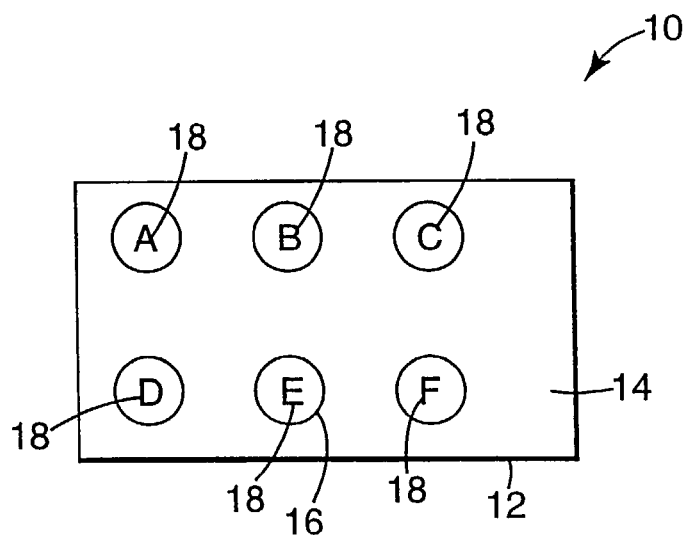
FIG. 2 is a perspective view of an oligonucleotide array manufactured in accordance with the methods of the present invention wherein each letter represents a different oligonucleotide.

With reference to FIG. 2, in a preferred embodiment, a variety of nucleic acids, such as oligonucleotides 18 (an oligonucleotide being denoted by a letter) are affixed to the substrate 12 at separate binding sites 16. The variety of oligonucleotides 18 on the substrate 12 permits a large number of potential binding events between reactants and target analytes in a sample.

The reactants may be affixed prior to, during or after reduction of the major surface or relaxation of the substrate. However, it is preferred to affix the reactants prior to reduction of the major surface or relaxation of the substrate in order to take advantage of the methods of the present invention wherein high reactant binding site densities may be achieved.

With reference to FIGS. 6b, 7b, 8b, and 9b, arrays of the present invention are capable of exhibiting high topographical surface areas. These high surface area arrays offer additional opportunities for increasing signal strength of the arrays. The undulated surfaces permit more reactants to be affixed to a given area versus binding reactants to a relatively flat surface. Also, in the case where reactants are affixed prior to relaxation of the substrate, the spatial relationship of the reactants to one another on the surface is fixed. Upon relaxation of the substrate, the surface of the coating becomes undulated, in effect, increasing the density of reactants with respect to the projected surface area but substantially maintaining their relative separation due to the topographical surface area. This spacing allows presentation of a high density of reactants or binding sites at or near the surface of the coating while minimizing potential steric crowding. This, in turn, facilitates rapid interaction kinetics with prospective analytes.

Figure 4:
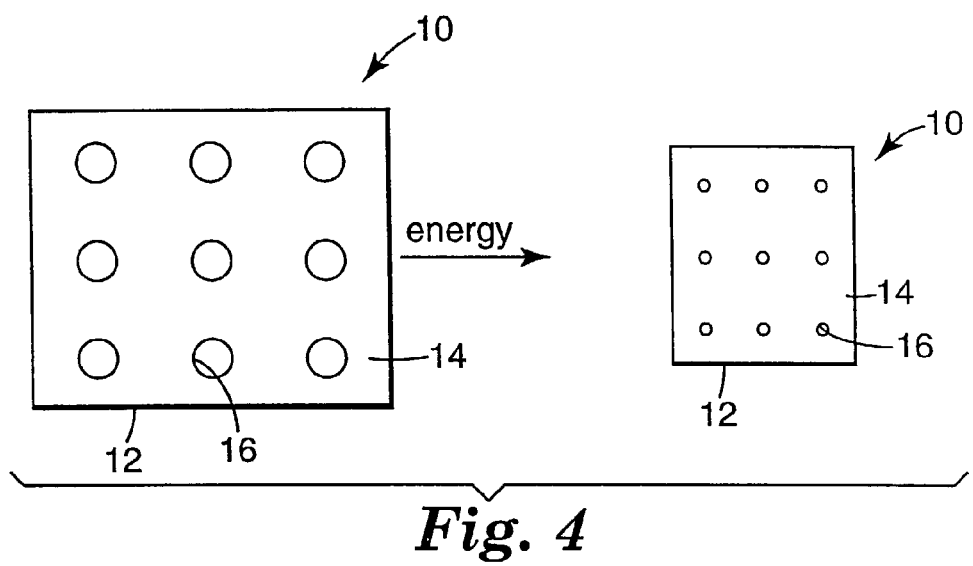
FIG. 4 illustrates an embodiment of the methods of the present invention.
Figure 5:
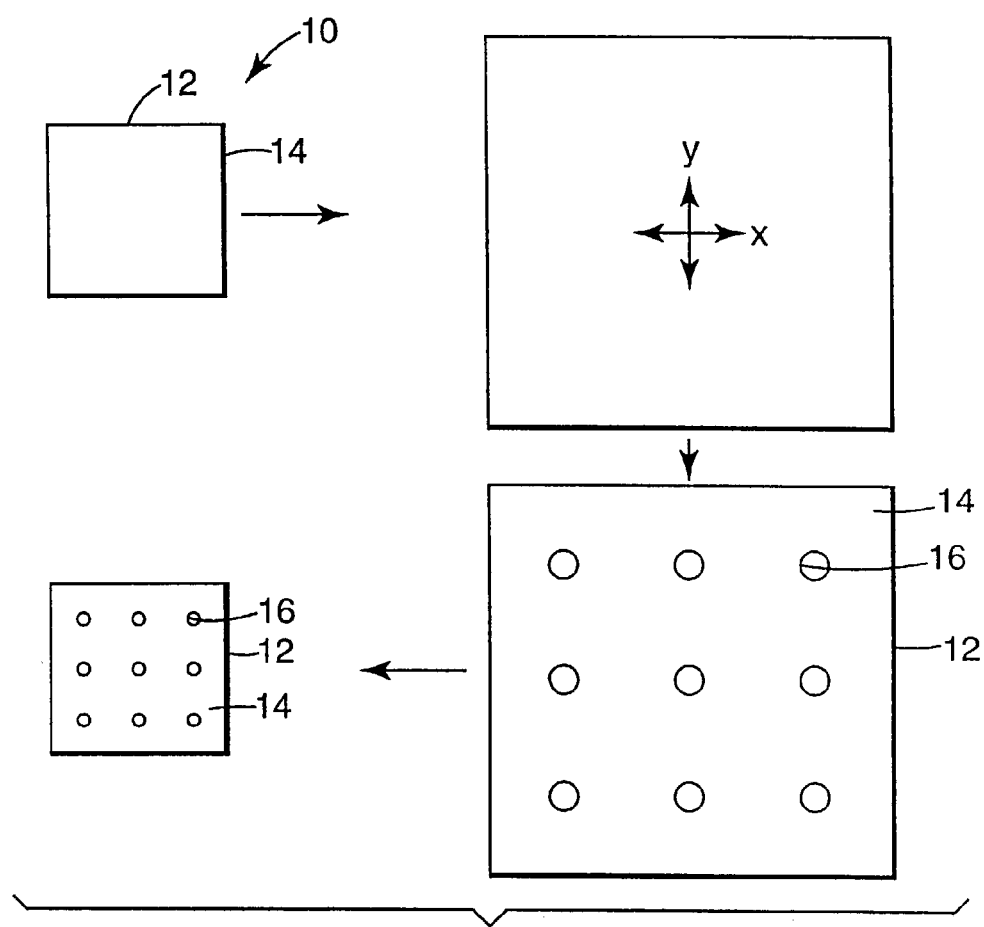
FIG. 5 illustrates another embodiment of the methods of the present invention.

With respect to the methods of the present invention and reference to FIGS. 4 and 5, the substrate 12 starting material is at least partially oriented. Oriented films exhibit an area shrinkage reduction that is dependent in part on the degree of elongation of the film during orientation thereof. In the methods of the present invention, the area shrinkage reduction is a measure of the area shrinkage of the film from its oriented, pre-shrunken dimensions to its dimensions after energy has been applied to shrink the film. For example, a 10 cm×10 cm (100 cm$^2$ area) film that shrinks fifty percent (50%) in the "x" direction and fifty percent (50%) in the "y" direction after the application of sufficient heat will be reduced to 5 cm×5 cm (25 cm$^2$ area), thereby exhibiting an area shrinkage reduction of seventy-five percent (75%). An area shrinkage reduction of about twenty-five percent (25%) is suitable for use in the present invention with an area shrinkage reduction of more than about seventy-five percent (75%) being most preferred because films exhibiting area shrinkage reductions of this magnitude are capable of achieving very high-density arrays, as more fully described below.

Referring to FIG. 5, the substrate 12 is prepared. In the case of elastomeric materials, the substrate 12 is stretched in the "x" and/or "y" direction and retained in the stretched condition. Processes for stretching an elastomeric material may include using a tentering device or stretching the material over a frame or mandrel. In most applications, a uniform stretching of the substrate in both the "x" and "y" configuration is preferred so that reactants may be affixed or bound to the substrate in parallel rows. However, other patterns of reactants may be desired, such as, for example, a fan shape array of reactants. Accordingly, the extent and pattern of stretching may be dependent on the desired shape of the finished array.

With reference to FIGS. 4 and 5, the surface of the substrate 12 need not be functionalized in order to affix reactants 22 thereto. However, depending on the mode of affixation, the substrate 12 may be further prepared by functionalizing the surface to create linking agents.

The type of functionalization will depend on the type of substrate and reactant(s). For example, in a preferred embodiment using an oriented film, such as oriented polyethylene, the linking agents are azlactone moieties. In addition to the azlactone copolymers set forth above, suitable azlactone functional compounds include those such as are disclosed in U.S. Pat. Nos. 4,485,236 and 5,149,806, the disclosures of which are incorporated herein by reference. One method of functionalizing the surface includes acid washing the substrate followed by the addition of a bis-amino molecule to create an amine-functional surface, to which azlactone-linking agents are affixed. The resulting functionalized surface is capable of affixing oligonucleotides. Other processes for functionalizing polymers are known in the art and are suitable to the extent they can be employed to create linking agents for affixation of reactants, for example, the heterobifunctional cross-linking agents disclosed in U.S. Pat. No. 5,436,147, the disclosure of which is incorporated herein by reference. The linking agents preferably remain substantially affixed to the substrate after reduction of the surface area of the major surface and further preferably are not substantially degraded by the reduction of the surface area. After functionalization, the substrate comprises a blank array, suitable for subsequent affixation of reactants.

One skilled in the art should also appreciate that a variety of approaches to rendering the surfaces of elastomeric materials chemically reactive are known and may be employed in the present invention to the extent their use creates linking agents on the substrate for subsequent affixation of reactants. The linking agents preferably remain substantially affixed to the substrate after reduction of the surface area of the major surface or relaxation of the substrate and further preferably are not substantially degraded by such reduction or relaxation. One example of such an approach for treating surfaces for biomolecule attachment is described in U.S. Pat. No. 5,258,041, incorporated herein by reference.

With reference to FIG. 3, reactants 22 are introduced to the substrate and preferably to the major surface for affixation to create binding sites 16. The modes of affixation may include, without limitation, physical means, such as for example, physically entrapping the reactants 22 within the substrate. With reference to FIGS. 1a and 1b, in a preferred embodiment of the present invention, reactants 22 are introduced to be affixed to the substrate 12 using a coating 15 of linking agents. The linking agents may be coated on the substrate 12 using any of the methods described above. Preferably, the coating 15 is at least partially adhered to the major surface 14 of the substrate 12. The substrate 12 may also be primed or otherwise treated prior to such coating step in order to enhance adhesion of the coating 15 to the substrate. Suitable primers are set forth above.

Regardless of how the reactants are affixed, any number of processes known in the art may be used to introduce the reactants 22 to the substrate, including on-chip or off-chip synthesis. Using such techniques, the methods of the present invention can be used to increase array site density by greater than a factor of 20. For the purpose of high throughput manufacturing, however, sophisticated miniaturized tools and methods, such as those used in on-chip and off-chip synthesis, may not be desired. Accordingly, large quantities of reactants may be deposited in a short period of time because the initial substrate size is relatively large, such as a substrate having a 4 cm×4 cm surface. The resulting binding sites formed may be relatively large, with areas, for example, of approximately 0.25 mm$^2$ to 1.0 mm$^2$ being suitable for use in the present invention. For example, the solutions containing the reactants 22 to be affixed may be simultaneously introduced by arrays of capillary tubes, by arrayed pipetting devices, or by an array of posts designed to transfer liquid droplets from a tray of reservoirs.

It is preferred that the reactants be introduced to the substrate in a known pattern for purposes of registration. The initial starting position of the reactant should be known in order to correlate this position with the final position once the substrate size has been reduced to the dimension which will be employed in conducting the assay. Each binding site may include a dye to assist in the correlation between initial starting point and the end point. Preferably, the dye has a different detection mode, e.g., light source, wavelength, etc., than the dye or indicator used for purposes of detecting binding events on the array.

With continuing reference to FIGS. 4 and 5, after affixation of the reactant(s) to the substrate, preferably the major surface thereof, or in certain instances, after functionalization of the substrate to create linking agents (not depicted), the substrate 12 is relaxed and the surface area of the major surface 14 of the substrate 12 is reduced by the application of energy, such as heat, in the case of oriented films and by the relaxation of the stretching force in the case of elastomeric materials. The number of binding sites 16 before and after size reduction is equivalent. However, the increase in density of reactants, binding sites 16 and linking agents, if present, may be dramatic. The arrays manufactured in accordance with the methods of the present invention are capable of having binding site densities of over 1,000 per cm$^2$. A preferred density is at least 25,000 per cm$^2$ and a most preferred density is over 60,000 per cm$^2$. Accordingly, the methods of the present invention permit the manufacturer to increase the density of binding sites from the initial affixation of reactants to the size reduced state by fairly substantial factors, such as 4, 10, and even over 20. With reference to FIG. 4, the area of each binding site 16 can be reduced by these same factors, thereby creating an increased density of reactant 22 at each site. This increased density of reactant 22 is advantageous where an increased signal for detection is desired when conducting an assay, for example when fluorescent, absorbent, or chemiluminescent species are used as reporters.

With respect to oriented films, the reduction is preferably effected by the application of heat. However, any mode that results in the reduction of the surface area of the major surface may be sufficient for purposes of this invention. Preferably, the mode of size alteration, such as the application of heat, does not substantially impair the activity of the reactants. The applicant has demonstrated that fairly high heat may be employed to shrink a substrate having oligonucleotides affixed thereto (approximately 150 degrees Celsius) without destroying the ability to have subsequent DNA hybridization occur with the oligonucleotides.

With respect to elastomeric materials, the surface area reduction may be achieved by releasing the force that is holding the material in the stretched condition. The substrate may be subsequently treated to hold the substrate in the reduced format. Alternatively, a backing or other physical means may be affixed to the substrate to hold it in the size altered format.

After size alteration of the substrate, the substrate, if desired, may be treated to retain the substrate in the reduced surface area state. Such treatment includes cross-linking the substrate. Alternatively, physical modes may be used, such as affixing a backing to the substrate.

The arrays manufactured by the methods of the present invention are useful in a variety of applications, including without limitation, gene sequencing, monitoring gene expression, gene mapping, disease detection, drug discovery, and combinatorial chemistry.

One skilled in the art will recognize that the methods of the present invention may be adapted for use on a mass production basis.

The following examples have been selected merely to further illustrate features, advantages, and other details of the invention. It is to be expressly understood, however, that while the examples serve this purpose, the particular ingredients and amounts used as well as other conditions and details are not to be construed in a manner that would unduly limit the scope of this invention.

EXAMPLE 1

Affixation of Pattern to Biaxially Oriented Film

This example serves to demonstrate a method of the present invention using a test pattern printed on a biaxially oriented heat shrink film substrate.

A repeating pattern of circular spots was printed on the surface of a roll of biaxially oriented polyethylene shrink film (Cryovac™ D-955 Film, W.R. Grace & Co., Duncan, S.C.) using standard flexographic printing methods. The pattern comprised a 34×32 square array of circular spots (0.5 mm diameter) spaced 1.0 mm apart center to center (100 spots per square centimeter). Following printing, a section of film containing the pattern was cut from the roll. The film was then placed on a hot plate with ; surface temperature of 155° C. The film was occasionally flipped with tweezers to provide even heat distribution during the shrink step. After observable shrinkage had ceased (approximately 2–3 minutes), the film was removed from the hot plate and allowed to cool. The resulting size of the pattern after the shrink step was approximately 0.77 cm×0.70 cm, with the spots decreased in size to 110 microns in diameter spaced approximately 225 microns apart, as measured under a microscope. The original spot density increased approximately 20 fold, from 100 spots per square centimeter to 2,000 spots per square centimeter.

EXAMPLE 2

Functionalization of Biaxially Oriented Film to Create Linking Agents

This example serves to demonstrate the covalent attachment of a linking agent to the surface of a biaxially oriented shrink film. The linking agent is used for subsequent attachment of reactants.

Carboxylic acid functionality was generated on the surface of polyethylene shrink film (Cryovac™ D-955, 75 gauge, W.R. Grace and Co., Duncan, SC) according to the procedure of Bentjen, et al. (Journal of Applied Polymer Science, Vol. 44, 1992, p. 965), incorporated herein by reference. A 5 cm×5 cm section of film was immersed in a chromic acid solution ($CrO_3/H_2O/H_2SO_4$) at 72° C. for 1 minute. The sample was washed with water (1×), nitric acid (10%, 1×), and water (1×). The sample of polyethylene shrink film was allowed to air dry at ambient temperature. Subsequently, it was immersed in a solution of dichloromethane (10 milliliters) containing diisopropylcarbodiimide (80 microliters, 50 mM, Aldrich Chemical Co.) and N-hydroxysuccinimide (60 mg, 50 mM). The solution containing the film was gently agitated for 30 minutes. O.O' Bis (2-aminopropyl)polyethylene glycol 800 (500 mg, Fluka Chemical Co.) was then added along with diisopropylethylamine (20 microliters, Aldrich). The solution was gently agitated for 18 hours at which time the polyethylene shrink film containing a hydrophilic linking amine group was removed and washed with dichloromethane (3×).

A 5 cm×5 cm section of the polyethylene shrink film prepared as described above was immersed in a solution (5% solids, methylethylketone, 25 ml) containing a copolymer of vinyldimethyl azlactone/dimethylacrylamide (60/40 wt/wt), prepared by typical solution polymerization method well-known in the art, such as that described in U.S. Pat. No. 4,304,705, incorporated herein by reference. The solution was gently agitated for 2 hours at room temperature. The polyethylene film was removed from this solution, washed with MEK (15 minutes) and allowed to air dry, thus generating a substrate including covalently attached linking agents.

EXAMPLE 3

Affixation of Reactant to Biaxially Oriented Film

This example demonstrates the covalent attachment of an oligonucleotide to the surface of the film prepared in Example 2.

Fluorescently labeled thymidine octamers were used to demonstrate covalent attachment to the azlactone functionalized film of Example 2. 3'-C3-amino-(thymidine)$_8$-5'-fluorescein isothiocyanate ($H_2N$-(T)$_8$-F ITC) and 3'-hydroxyl-(thymidine)$_8$-5'-fluorescein isothiocyanate (HO-(T)$_8$-FITC) were purchased from Genemed Synthesis, Inc., South San Francisco, Calif. The lyophilized samples (5 O.D.,57 nanomoles) were reconstituted in deionized water (0.5 ml) and stored frozen. Solutions of oligonucleotide (20 nanomole/ml) were prepared from this stock solution by dilution into phosphate buffer (50 mM, pH 8.5).

The solutions were manually spotted in adjacent rows on the surface of the film using a microcapillary (4 microliter Microcap, Drummond Scientific Co., Broomall, Pa.) by briefly contacting the surface of the film with the opening of the microcapillary, depositing approximately 50 nanoliters of solution per spot. The spotted film was placed in a covered petri dish overnight (16 hours) at room temperature. Subsequently, the film was placed in a solution of ethanolamine (50 mM in water). After 45 minutes, the film was removed and washed in water (2×) followed by washing (30 minutes) in a solution of phosphate buffered saline containing 0.05% Tween 20. The film was washed again in water (2×), then air-dried. Dust was removed from the surface of the film using a can of Effa Duster™ (Ernest F. Fullam, Inc., Latham, N.Y.). The film was hydrated with pH 7.0 phosphate buffer and observed under a fluorescence microscope equipped with a FITC/TRITC filter set (Chroma Technology). Fluorescence was observed in the row of spots corresponding to the amine-terminated oligonucleotide solution. Each spot was approximately 700 microns in diameter, corresponding to an area of 0.38 mm$^2$. Extremely faint fluorescence was observed in the row corresponding to the hydroxyl terminated oligonucleotide, thus demonstrating a high degree of covalent attachment of the amine-reactive oligonucleotide with the azlactone linking agent.

A hot plate was heated to a surface temperature of 155° C. To prevent sticking to the metal plate during the shrinkage step, a silicone film (0.040", 3M Co.) was placed on the surface of the hot plate. The film containing attached oligonucleotide was then placed on the silicone film and allowed to shrink. The film was occasionally flipped with a forceps to provide uniform heating. When no further shrinkage was observed, the film was removed from the hot plate and allowed to cool. The film was hydrated with pH 7.0 phosphate buffer and observed under a fluorescence microscope equipped with a FITC/TRITC filter set.

After shrinkage, the spot size had been reduced to an area of 0.023 mm$^2$. Correspondingly, the intensity of the spot is significantly increased due to the increased local concentration of the labeled octamer, which is further demonstrated in the following examples.

EXAMPLE 4

Introduction of Reactants to Substrate Using Capillary Tubes

This example serves to demonstrate a method of the present invention using aligned capillary tubes for simultaneous affixation of a reactant on a substrate prepared in accordance with Example 2. This example also demonstrates increased concentration of fluorophore at each array site after shrinkage.

A linear assembly of 20 glass capillaries (100 micron inner diameter, 300 microns outer diameter, 500 micron center to center spacing, approximately 300 cm long) was assembled in registration at the proximal ends of the tubes. The distal ends of the capillaries were placed in a solution of 5((5-aminopentyl)thiourcidyl) fluorescein (100 micrograms/ml, Molecular Probes, Eugene, Oreg.) in Na2SO4

(1M)/AMPSO (50 millimolar) buffer (pH 9.5). After the capillaries had completely filled, the proximal end of the capillary assembly was briefly contacted to the surface of an azlactone derivitized film prepared as described in Example 2. A small amount of solution was simultaneously deposited from the ends of each capillary onto the surface of the film upon removal of the assembly from the film. The film was then placed in a covered petri dish and allowed to stand overnight (16 hours). The film was washed in phosphate buffer (50 mM, pH 8.5) and allowed to air dry. The film was then placed on a microscope slide, hydrated with a drop of phosphate buffer, and covered with a glass cover slip. The film was observed under a fluorescence microscope as described in Example 3. The microscope was equipped with a CCD camera (Photometrics, Inc.), which was used to quantify the fluorescence intensity of each spot. The intensity was quantified by capturing an image from the CCD followed by importing the signal into image processing software (UTHSCSA Image Tool V. 2.O, University of Texas). The average fluorescence intensity of a spot was determined using the line profile function of the software. Distances were determined using the distance function calibrated against a, 100 micron grid.

Before shrinkage, each spot measured approximately 420 microns in diameter, with a center to center spacing of 500 microns. Average fluorescence intensity for the spots was 4940 relative light units (RLU). The film was then shrunk according to the procedure outlined in Example 1. After shrinkage, images were acquired using identical parameters as were used for the pre-shrunk state. Average intensity of the spots had increased to 22,500 RLU, demonstrating an increased concentration of fluorophore within each spot after the shrink step. Correspondingly, the spot size decreased to approximately 90 microns with a center to center spacing of approximately 120 microns.

EXAMPLE 5

Introduction of Reactants to Substrate Using Patterned Posts

This example serves to demonstrate a method of the present invention using an array of posts for the simultaneous transfer and deposition of reactant solution to the surface of the film substrate.

A 6×6 array of square posts was machined from a 1 inch×1 inch aluminum block having the following dimensions: post height=1.8 mm, width=0.75 mm, spacing=4.0 mm center to center. A small notch having an internal angle of approximately 90 degrees was cut from the tip of each post. A tray having circular reservoirs of 3.1 mm diameter, 2.0 mm depth, and 4.0 mm center to center spacing was drilled from a block of polyethylene. A solution of 5((5-aminopentyl)thioureidyl) fluorescein (described above) was placed in each reservoir (12 microliters per reservoir). The tips of the post array were then dipped in the solutions. Upon removal of the array, a small droplet of solution remained on each post tip. The post array was then contacted with the surface of an azlactone functionalized film. The film was allowed to stand, washed, and imaged as described above. The spots were observed to be approximately 800 microns in diameter, with a center to center spacing of 4.0 mm. Average fluorescence intensity was determined to be 3960 RLU. After shrinking the film as described above, the intensity was observed to increase to a relative fluorescence of 19,130 RLU, with a decrease in diameter to approximately 200 microns and a decrease in center to center spacing to approximately 860 microns.

EXAMPLE 6

DNA Hybridization on Heat Shrink Film Substrate After Reduction of Surface Area of Substrate This example serves to demonstrate DNA hybridization on a modified shrink film containing covalently attached oligonucleotide.

A 2 cm×2 cm section of azlactone functionalized film was prepared in accordance with Example 2. Solutions of oligonucleotide were prepared as described in Example 3 Using the following sequences: 3'-(C3 amino)-TCC TAA GGC CCA ATA-5' ("match") and 3'-(C3 amino)-CTT CGG AAT TTG GCG-5' ("mismatch") (Genemed Synthesis). The solutions were spotted in adjacent rows and allowed to react as described in Example 3. After the reaction, the film was placed on a hot plate and allowed to shrink as described in Example 1.

The film was then placed in a solution of 5×SCC (0.75 M NaCl, 0.075 M sodium citrate, pH 7.0) containing L-sarcosine (0.1%), casein (1%), and sodium dodecyl sulfate (0.02%) for 5 minutes. The film was then transferred to a small vial containing 300 microliters of the above solution containing 3'-(FITC)-TAT TGG GCC TTA GGA-5'-OH (15 nanomoles/ml). The hybridization reaction was gently agitated on a rotary mixer for 16 hours at 25 C. The film was removed from the hybridization solution and washed with 5×SCC (2×). The film was then placed on a microscope slide and hydrated with a drop of phosphate buffer (50 millimolar, pH 7.0). A cover slip was placed on the hydrated film.

The film was observed under a fluorescence microscope equipped with a fluorescein filter set. Fluorescence was observed in the row of spots containing immobilized "match" sequence (3'-(C3 amino)-TCC TAA GGC CCA ATA-5'). No fluorescence was observed in the row corresponding to the "mismatched" sequence (3'-(C3 amino)-CTT CGG AAT TTG GCG-5'), thus demonstrating that an oligonucleotide can be covalently attached to the surface of a biaxially oriented film, heat can be applied to shrink the film, and a complimentary oligonucleotide can be hybridized to the oligonucleotide on the resulting film.

EXAMPLE 7

Prophetic Example to Functionalize an Elastomeric Substrate

This example serves to illustrate a method of rendering the surface of an elastomeric rubber substrate chemically reactive.

In this example, a sheet of rubber (obtained from a variety of sources, for example Lloyd Manufacturing, Warren, R.I.) may treated to convert a small percentage of double bonds in the polymer backbone to epoxides. For this example the sheet may contain carbon black to reduce background fluorescence. Epoxidization can be achieved via several routes that are well-known in the art, including treatment with perbenzoic, pepthallic, and peracetic acid. It is well-known in the art that epoxides can be ring opened with a variety of nucleophiles, including water, alcohols, hydrogen halides, thiols and amines. Epoxidized rubber, prepared by one of the procedures outlined above may be treated with an excess of O.O' Bis (2-aminopropyl)polyethylene according to the procedure outlined in Example 2. If necessary, the reaction may be heated to promote ring opening of the epoxide. The amine-functionalized rubber may then treated with a copolymer of vinyldimethyl azlactone/dimethylacrylamide as described in Example 2, generating a highly functional surface that is reactive towards nucleophilic moieties, for example amine terminated oligonucleotides. Alternatively, if a lower degree of substitution is needed, the epoxidized rubber may be treated directly with amine terminated oligonucleotide in a single step.

EXAMPLE 8

Prophetic Example of Affixation of Reactant to Elastomeric Substrate

The functionalized elastomeric substrate formed as described in Prophetic Example 7 may be mechanically elongated in either the "x" or "y" direction or simultaneously in both "x" and "y", for example by placing the substrate over a frame or mandrel. Reactants in the form, for example, of oligonucleotides, may be applied to the elongated elastomer. A variety of methods can be employed for forming the array, including delivery through an array of tubes, needles, inkjets, pens, or via transfer from an array of reservoirs using a stamp. After the solutions have been deposited on the surface and the biomolecules have been allowed to react, the mechanical force is removed, thereby reducing the size of the array while at the same time increasing the local concentration of reactants within each site on the array.

EXAMPLE 9

Registration of Reactants on Substrate

This example serves to demonstrate a method for locating the reactants after affixation to a biaxially oriented film using a reporter molecule incorporated within each array site. The reporter molecule used for locating the array elements is detected at a wavelength that is different than the reporter molecule used in the assay.

A solution "1" containing 5-(2-aminoethylamino)-1-napthalene (EDANS, 200 micromolar in pH 8.5 phosphate buffer) was prepared. A second solution "2" containing 3'-C3-amino-(thymidine)$_8$-5'-fluorescein isothiocyanate ($H_2N$-$(T)_8$-FITC) was prepared by dilution of the stock solution from example 3 into the EDANS solution "1" (5 micromolar final $H_2N$-(T)8-FITC concentration.) Rows of spots from solution "1" were generated on the film using a microcapillary spotter as described in Example 3. Within each row, a random space was left open, which was subsequently spotted with solution "2". In this manner rows of spots were generated where all spots contained EDANS and one spot contained EDANS plus attached fluorescein-labeled oligonucleotide. The spotted film was placed in a covered petri dish for one hour, at which time it was removed and washed with water, dried, and shrunk as described in Example 1. After the shrink step, the film was observed under a fluorescence microscope first using a bandpass excitation filter (350+/−20 nm) and a longpass emission filter set (>420 nm, Chroma Technology). Using this filter set, EDANS fluorescence from each spot was observed and the image and position of each spot recorded using a CCD camera and imaging software as outlined in Example 4. The film was then observed using a FITC/TRITC filter set (Chroma Technology). Only the single spots within each row containing attached $H_2N$-$(T)_8$-FITC were observed. An "overlay" of the two images provides the location of the spots containing the labeled oligonucleotide, thus demonstrating that a reporter molecule can be incorporated into each array element, serving to determine the spatial location of each spot in the array. This information is then stored and used to determine the identity of the of spots in which a second reporter is located, for example a reporter bound at an array site to sites during a hybridization reaction.

EXAMPLE 10

Preparation of Copolymers Comprising Linking Agents

Preparation of copolymers is readily accomplished by procedures well known in the art, such as procedures taught in U.S. Pat. No. 4,304,705, incorporated herein by reference. The following is a typical example: Into a reaction vessel equipped with a stirrer, thermometer, reflux condenser, means for heating, and means for maintaining a nitrogen atmosphere in the vessel were charged (parts by weight) 2-vinyl-4,4-dimethyl-2-oxazolin-5-one (vinyldimethylazlactone 12 parts), N,N-dimethylacrylamide (28 parts), 2-butanone (60 parts) and azobisisobutyronitrile (0.15 parts). The solution was sparged with nitrogen and heated at 55° C. with agitation for 24 hours. After this time the percent polymer solids in the solution obtained, as determined by a standard gravimetric procedure, was 39.8%, indicative of 100% conversion of monomers to polymer. This polymer solution was then diluted to lower % solids solutions with additional 2-butanone or other solvents for the preparation of coating solutions.

In a similar manner, other polymers having different ratios of monomers, different comonomers, or different linking agent monomers can be prepared and used in the invention.

EXAMPLE 11

Priming and Coating Methods

This example serves to demonstrate methods for priming the surface of substrate as well as methods for providing uniform, thin coatings comprising linking agents on the substrates.

For the Examples 11a–11i described in Table 1, a roll of oriented substrate film was either unprimed (none), corona treated (Cr), or ammonia-plasma treated (AP) according to techniques well known in the art prior to coating. Priming with Polyethylenimine (PEI, average $M_w$ ca. 750,000, 50 wt. % solution in water) (Aldrich) was accomplished by diluting the stock solution to 0.05% w/w with methanol followed by extrusion die coating onto the appropriate film substrate.

For coating, the copolymers comprising linking agents prepared as described in Example 10 were diluted with appropriate solvents to provide the coating solutions, typically less than 10% solids by weight, preferably <5% solids. Coating methods used were: (1) Extrusion die coating, "E"; and (2) Reverse-roll gravure, "G". Optionally, the coating solution was formulated with a cross-linker prior to coating. For extrusion coating, this was accomplished by utilizing two reservoirs, one for the polymer solution and one for the crosslinker solution. The solutions were pumped through an in line mixer just prior to entering the coating die. For each example, the solvent was removed from the coating by passage of the film through an oven heated to 38° C. for approximately 1 minute.

TABLE 1

| Exp. | Substrate | Priming | Copolymer Coatings used | Solvent (% Solids) | Coating Method | Crosslinker (wt. %) |
|---|---|---|---|---|---|---|
| 11a | A | None | 70:30 p(DMA/VDM) | MEK (1.5) | E | ED (10%) |
| 11b | A | Cr | 70:30 p(DMA/VDM) | MEK (1.0) | E | ED (10%) |
| 11c | A | Cr | 70:30 p(DMA/VDM) | MEK (1.5) | E | ED (10%) |
| 11d | B | AP | 70:30 p(DMA/VDM) | IPA (5.0) | G | None |
| 11e | A | None | 50:30:20 p(BA/DMA/VDM) | MEK (1.5) | E | None |
| 11f | B | Cr | 70:30 p(DMA/VDM) | IPA (1.0) | G | None |
| 11g | B | None | 70:30 p(DMA/VDM) | IPA (1.0) | G | None |
| 11h | A | Cr/PEI | 70:30 p(DMA/VDM) | MEK (1.5) | E | None |
| 11i | C | Cr | 70:30 p(DMA/VDM) | MEK (1.0) | E | ED (2.5%) |

A = Biaxially oriented polyethylene, Cryovac D955 1.0 mil, Sealed Air Co., Duncan, SC.
B = Biaxially oriented polyethylene, Cryovac D955 0.6 mil, Sealed Air.
C = Biaxially oriented polyethylene, Clysar 1.0 mil, DuPont Co., Wilmington, DE.
Copolymers: DMA = dimethylacrylamide; VDM = vinyldimethylazlactone; BA = butyl acrylate
Solvents: MEK = 2-butanone; IPA = isopropyl alcohol
Cross-linker: ED = 1,2-ethylenediamine (Aldrich);
Other abbreviations described in Methods above

EXAMPLE 12

Formation of Undulated Surface

This example serves to demonstrate the formation of undulated surfaces from a coating comprising linking agents on the substrate.

Figure 6B:
FIG. 6b is an SEM of the coated substrate of FIG. 6a subsequent to relaxation thereof.

A section of coated film from Example 11a was relaxed according to the procedure outlined in Example 3. SEM images were obtained using standard preparation techniques (scanning electron microscope, Model XL 30 Series, Philips Electronic Instruments, Mahwah, N.J.). Briefly, the samples were placed on a small amount of carbon tape on the mounting stub so that it contacted only the underside of the sample at opposing corners. The mounted samples were then placed in a sputter chamber (Hummer XP, Anatech LTD) for a time sufficient to deposit approximately 7–9 nm of gold coating. Samples were examined under an accelerating voltage of 15 kV at a spot size of 4 with the samples at a 40 degree tilt. Images for a sample having an oriented and a relaxed substrate sample thereof were obtained (FIGS. 6a and 6b, respectively). FIG. 6a shows that the coating comprising linking agents is substantially smooth prior to shrinking. FIG. 6b demonstrates that the linking agent coating has formed an undulated surface. Examples 11b, 11c, 11d, 11f, 11g, 11h, 11i were also shown to form undulated surfaces.

EXAMPLE 13

Stability of Coatings

This example serves to demonstrate improved adhesion of the linking agent coating subsequent to relaxation of the substrate.

Stability of coatings on coated sample of Example 11c with respect to washings at high pH, high temperatures, and in the presence of surfactants was studied in the following manner.

A 50 mM sodium phosphate buffer was prepared at pH 8.38 with 1% (%/i) sodium dodecyl sulfate (SDS) in DI water. Oriented and relaxed pieces of the above sample were immersed in the above buffer solution at 80° C. for 5 hours.

The samples were analyzed using attenuated total reflectance (ATR) (Model Bomem MB 102, Golden Gate Diamond ATR Series, Graseby Specac) IR spectroscopy to detect the presence of the coating. The relaxed sample contained the following absorbance bands consistent with the presence of copolymer coating: 1618 (strong, broad band due to amide carbonyl), 1498, 1398, 1355 (medium, sharp bands) cm$^{-1}$. These bands were absent in the oriented sample, thus indicating that the process of relaxing using heat, improves the adhesion of the coating to the substrate under these conditions.

EXAMPLE 14

PEI Coating

This example serves to demonstrate a method for making a PEI undulated coating.

Figure 7A:
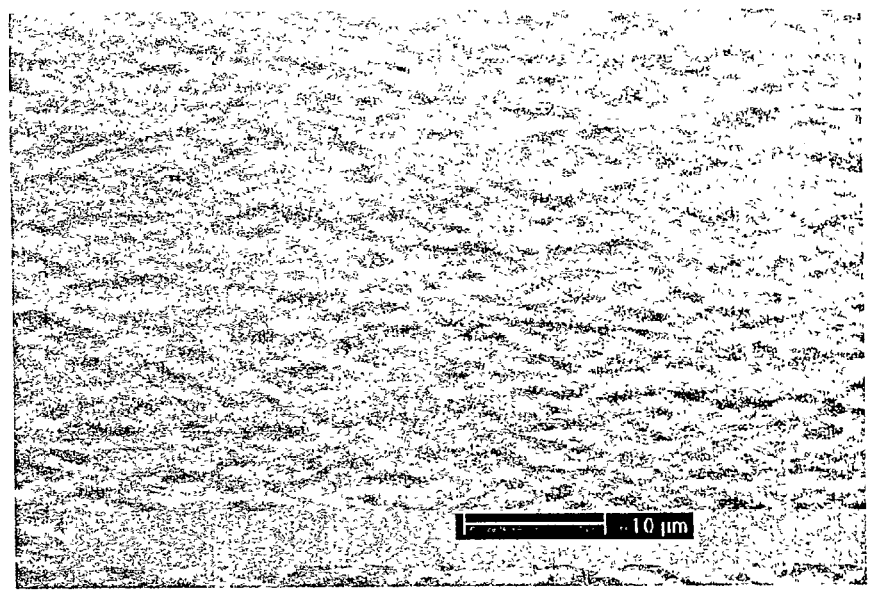
FIG. 7a is an SEM of a relaxed substrate coated with polyethylenimine.

A sample of oriented film (Cryovac D955, 1.0 mil) was corona (Cr) treated and coated with a 0.05% (w/w) solution of PEI in methanol (Aldrich) as described in Example 11. A section of this sample was relaxed according to the procedure outlined in Example 3. The SEM of the coating is shown in FIG. 7a, demonstrating that the coating is substantially smooth. Accordingly, an undulated surface did not form.

Figure 7B:
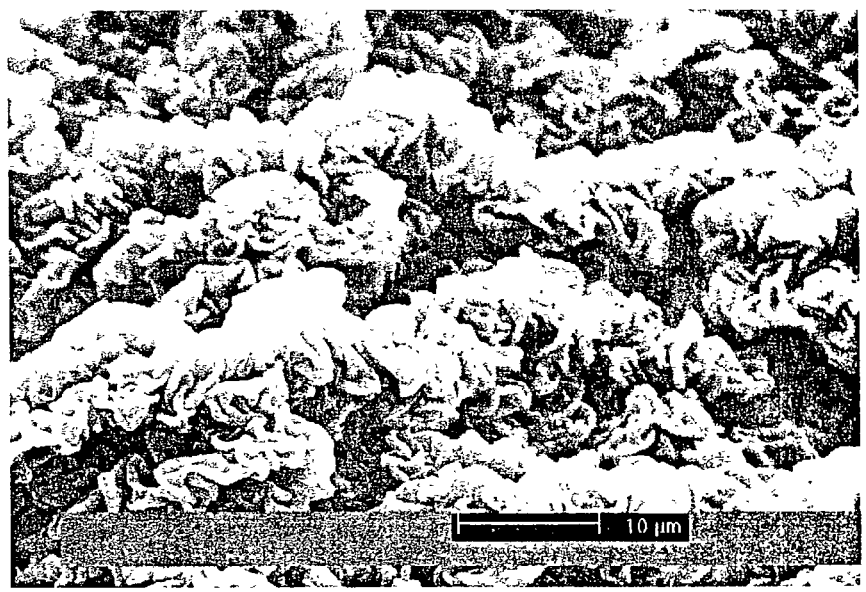
FIG. 7b is an SEM of a relaxed substrate coated with dimethylacrylamide/vinyldimethylazlactone copolymer over-coated with polyethylenimine.

In order to prepare a PEI surface that was undulated, the azlactone/dimethylacrylamide coated substrate of Example 11a was extrusion over-coated with a 0.3% (w/w) solution of linear Polyethylenimine (PEI M$_n$ ca. 423) (Aldrich) in methanol. A section of this sample was relaxed according to the procedure outlined in Example 3. The SEM of this multilayer coating is shown in FIG. 7b, demonstrating that the coating of PEI linking agent is present in an undulated surface.

EXAMPLE 15

Carboxylated Polyvinylchloride Coating

This example demonstrates an additional polymer coating containing linking agents that formed the undulated surface of the present invention.

Figure 8B:
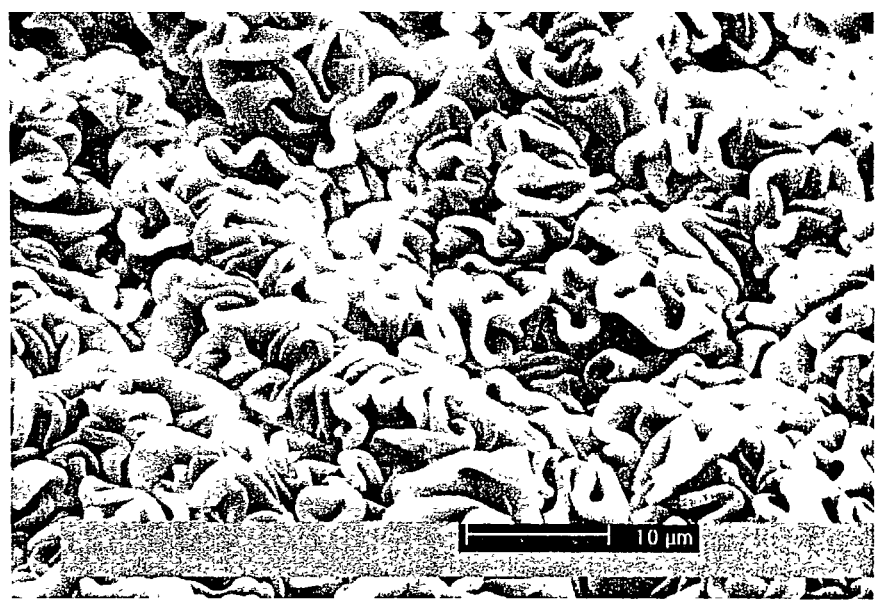
FIG. 8b is an SEM of the coated substrate of FIG. 8a subsequent to relaxation thereof.

A 1% (w/w) solution of carboxylated polyvinylchloride (1.8% carboxylated) (Aldrich) was made in tetrahydrofuran (THF) (Aldrich), with and without 1% DI water. These two solutions were hand-coated on the shrink film (Cryovac D955, 1.0 mil) at a wet of thicknesses of 0.005 inch, 125 microns. After coating the solvent was allowed to evaporate at room temperature for approximately 20 minutes. The oriented and relaxed samples for the samples coated without water were analyzed using SEM techniques. The micrographs showed that before relaxation, a smooth coating was present (FIG. 8a), whereas after relaxation an undulated surface was observed (FIG. 8b). The coating formed from the solution containing water also formed undulations.

EXAMPLE 16

Variation of Polymer Glass Transition Temperature

This example serves to demonstrate that a polymer containing linking agents having a glass transition temperature substantially lower than the glass transition ($T_g$) temperature of the substrate may not form undulations.

Figure 9A:
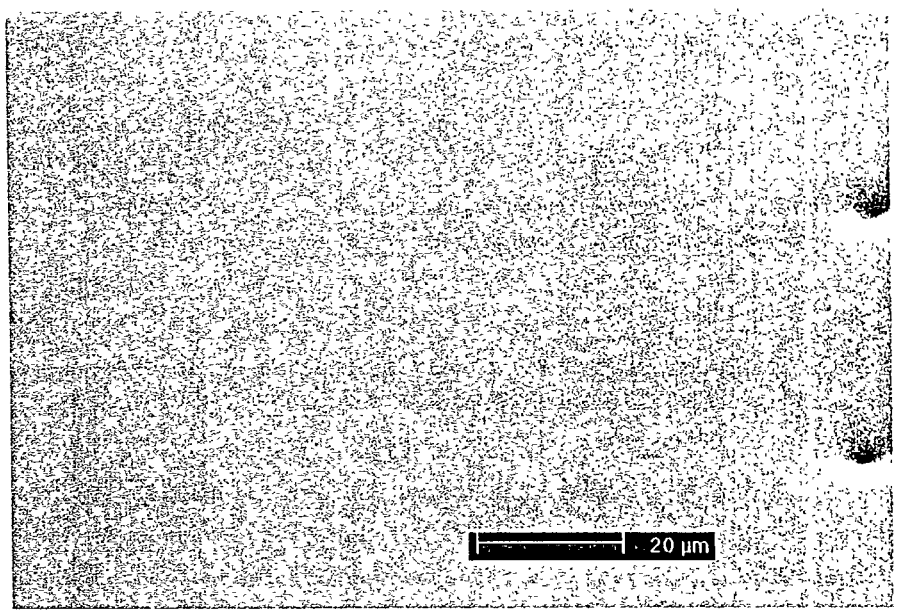
FIG. 9a is an SEM of a substrate wi trate.
Figure 9B:
FIG. 9b is an SEM of a substrate with a higher glass transition temperature copolymer than that of FIG. 9a, subsequent to relaxation of the substrate thereof.

A section of the coated film of example 11e was relaxed according to the procedure outlined in Example 3. The ($T_g$) of the copolymer used in this example was calculated to be approximately 0° C. The SEM of the coating is shown in FIG. 9a, demonstrating that the low $T_g$ copolymer forms a substantially smooth surface. In comparison, FIG. 9b depicts the SEM of the relaxed film of example 11d, where the $T_g$ of the copolymer was measured to be 110° C. by modulated differential scanning calorimetry (MDSC 2920, TA Instruments, Inc., New Castle, Del.). This sample formed an undulated surface.

EXAMPLE 17

Comparison of Oligonuclotide Hybridization on Glass Microscope Slides and Coated Shrink Film This example demonstrates enhanced signal obtained during an oligonucleotide hybridization utilizing a coated film of the present invention.

The procedure of Guo et. al. (Nucleic Acids Research, 1994, Vol. 22, No. 24) was used to prepare a reactive surface on a glass microscope slide. A slide treated with aminopropyltrimethoxy silane (Newcomer Supply, Middletown, Wis.) was immersed in 1,4 phenylene diisothiocyanate (0.2% solution in 1:9 pyridine:dimethylformamide). After two hours, the slide was rinsed with methanol (2×) and acetone (2×) followed by air drying. Two sections (1 inch by 1 inch) of shrink film coated with azlactone/dimethylacrylamide copolymer as described in Example 11 c were used in the subsequent steps.

Solutions of the three oligonucleotides (Genosys, The Woodlands, Tex., 250 mM in AMPSO buffer, pH 9.0) were prepared as described in Example 4 followed by spotting in adjacent rows using a capillary tube as described in Example 3 (Row 1=FITC labeled, row 2="match", row 3="mismatch"). After spotting, the glass and film samples were placed in a covered, humidified petri dish. After two hours, the samples were rinsed with distilled water, AMPSO buffer (50 mM, pH 9.0), distilled water, SDS (0.1% in water), and distilled water. One of the shrink film samples was relaxed according to the procedure in Example 1. FITC labeled oligonucleotide complimentary to the immobilized "match" row of spots was hybridized to the glass, oriented film, and relaxed film according to the procedure in Example 6 by placing a small drop of the hybrizidation solution onto each sample followed by addition of a cover slip. The samples were allowed to hybridize for 30 minutes in a 45° C. incubator. After hybridization, the samples were rinsed as described above. Fluorescence intensity for each row of spots was measured using a raster scanning device equipped with a 488 nanometer laser, fluorescein filters, and a photomultiplier tube. Average intensities expressed as relative light units (RLU) were measured. Detector gain adjustments were necessary for the film samples, which saturated the detector under the conditions used to measure the glass slide. A gain-dependent conversion factor was used to calculate normalized RLU values for the three samples. The following table summarizes the results of this experiment. The results clearly show an increase in intensity for the coated film samples due to a higher concentration of reactants. A further 10× enhancement results from relaxing the sample due to increased density of reactants.

| sample | Row 1-FITC labeled (RLU) | Row 2-"match" (RLU) | Row 3-"mismatch" (RLU) |
|---|---|---|---|
| Glass microscope slide | 198 | 75 | No signal |
| Unshrunk film | 15,100 | 14,100 | No signal |
| Shrunk film | 165,000 | 162,000 | No signal |

What is claimed is:

1. An array of reactants, comprising a relaxed oriented substrate having directly attached thereon, optionally by a linking agent, at each of a plurality of distinct binding sites a reactant and a label, wherein the structures of the reactants are identifiable by the discrete location of their binding sites, and wherein the amount of the label attached at each binding site is proportional to the amount of reactants attached at that binding site.

2. The array of claim 1, which is a one-dimensional array.

3. The array of claim 2, in which the substrate is a solid phase synthesis support comprising polyethylene.

4. The array of claim 1, which is a two-dimensional array.

5. The array of claim 1, in which the substrate is a plastic sheet.

6. The array of claim 1, in which the directly attached compounds are polynucleotides.

7. The array of claim 6, in which the polynucleotides are covalently attached to the substrate, optionally by way of a linking agent.

8. The array of claim 7, in which the polynucleotides are covalently attached to the substrate via their 5' or 3' terminal nucleotide.

9. The array of claim 7, in which each immobilized polynucleotide is independently 6 to 20 nucleotides in length.

10. The array of claim 9, in which all of the directly attached polynucleotides are the same length.

11. The array of claim 9, which comprises a complete set of polynucleotides 6–10 nucleotides in length.

12. The array of claim 1, in which the label comprises a fluorophore.

13. The array of claim 6, in which the label is a fluorescently-labeled polynucleotide.

14. The array of claim 13, in which the fluorescently-labeled polynucleotide directly attached, optionally by a linking agent, at each binding site has the same nucleotide sequence as the polynucleotide directly attached, optionally by a linking agent at that binding site.

15. The array of claim 13, in which the same fluorescently-labeled polynucleotide is directly attached, optionally by a linking agent, at each binding site.

16. A method of making an array of reactants, comprising the steps of:
   (i) directly attaching, optionally by a linking agent, at a first binding site of an oriented substrate a first reactant and a first label;
   (ii) directly attaching, optionally by a linking agent, at a second binding site of the substrate a second reactant and a second label; and
   (iii) relaxing the substrate after attaching the first reactant and the first label.

17. In a method of making an array of polynucleotides by directly attaching, optionally by a linking agent pre-synthesized polynucleotides at a discrete binding site on an oriented substrate, the improvements comprise directly attaching, optionally by a linking agent an amount of a label at each binding site that is proportional to the amount of polynucleotide attached at that binding site, and relaxing the oriented substrate after attaching the pre-synthesized polynucleotides at the discrete binding site.

18. In a method of making an array of reactants by in situ synthesis, the improvements comprise directly attaching optionally by a linking agent at each binding site of the array an amount of a label that is proportional to the amount of a product of the in situ synthesis directly attached, optionally by a linking agent, at that binding site, and relaxing the substrate after attaching the label.

19. A method of increasing the accuracy of an array-based assay comprising:
   contacting an array according to claim 1 with an analyte compound that is capable of generating an assay signal upon interacting with a compound of an array.

* * * * *

UNITED STATES PATENT AND TRADEMARK OFFICE
CERTIFICATE OF CORRECTION

PATENT NO. : 7,189,842 B2
APPLICATION NO. : 10/167204
DATED : March 13, 2007
INVENTOR(S) : Kurt J. Halverson It is certified that error appears in the above-identified patent and that said Letters Patent is hereby corrected as shown below:

Title Page
Item [56], References Cited, OTHER PUBLICATIONS, Delete "Analysis,"," and insert -- Analysis," --, therefor.

Column 3
Line 14, After "subsequent" insert -- attachment of reactants. The surface area of the substrate surface may be reduced, --.

Column 4
Line 17, Delete "wi trate." and insert -- with a low glass transition temperature copolymer subsequent to relaxation of the substrate. --, therefor.
Line 67, Delete "Compounds," and insert -- compounds, --, therefor.

Column 5
Line 7, Delete ""x, y"" and insert -- "x", "y" --, therefor.

Column 6
Line 50, Delete "nitrites," and insert -- nitriles, --, therefor.
Line 55, After "coating" insert -- 15 --.
Line 57, After "array" insert -- 10 --.

Column 13
Line 3, Before "surface" delete ";" and insert -- a --, therefor.
Line 67, Delete "($H_2N$-$(T)_8$-F ITC)" and insert -- ($H_2N$-$(T)_8$-FITC) --, therefor.

Column 14
Line 66, Delete "5((5-aminopentyl)thiourcidyl)" and insert -- 5((5-aminopentyl)thioureidyl) --, therefor.
Line 67, Delete "Na2SO4" and insert -- $Na_2SO_4$ --, therefor.

Column 15
Line 23, After "against" delete "a," and insert -- a --, therefor.

Column 16
Line 15, Delete "Using" and insert -- using --, therefor.

Column 17
Line 48, Delete "$H_2N$-$(T)8$-FITC" and insert -- $H_2N$-$(T)_8$-FITC --, therefore.

UNITED STATES PATENT AND TRADEMARK OFFICE
CERTIFICATE OF CORRECTION

PATENT NO. : 7,189,842 B2
APPLICATION NO. : 10/167204
DATED : March 13, 2007
INVENTOR(S) : Kurt J. Halverson It is certified that error appears in the above-identified patent and that said Letters Patent is hereby corrected as shown below:

Column 18
Line 6, After "of the" delete "of".
Line 63, Delete "crosslinkcr" and insert -- crosslinker --, therefor.

Column 20
Line 30, After "1%" delete "(%/i)" and insert -- (w/w) --, therefor.

Column 21
Line 44, Delete "Oligonuclotide" and insert -- Oligonucleotide --, therefor.

Column 22
Line 8, Delete "hybrizidation" and insert -- hybridization --, therefor.

Signed and Sealed this

Fourteenth Day of August, 2007

JON W. DUDAS
*Director of the United States Patent and Trademark Office*